United States Patent
Hoffman et al.

(10) Patent No.: US 7,253,294 B2
(45) Date of Patent: *Aug. 7, 2007

(54) ISOLATION OF LUTEIN FROM ALFALFA

(75) Inventors: Mark Hoffman, Lakeville, MN (US); David Baugh, Plymouth, MN (US); Michael Ahern, St. Paul, MN (US); David Walsh, Hollywood, SC (US)

(73) Assignee: Nu-Tein Co., Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/463,193

(22) Filed: Aug. 8, 2006

(65) Prior Publication Data

US 2006/0293543 A1 Dec. 28, 2006

Related U.S. Application Data

(63) Continuation of application No. 10/696,730, filed on Oct. 29, 2003, now Pat. No. 7,109,361, which is a continuation-in-part of application No. 10/688,776, filed on Oct. 17, 2003, now abandoned.

(60) Provisional application No. 60/452,565, filed on Mar. 7, 2003.

(51) Int. Cl.
  *C11B 1/00* (2006.01)
(52) U.S. Cl. .......................................... 554/8
(58) Field of Classification Search ............... None
  See application file for complete search history.

(56) References Cited

U.S. PATENT DOCUMENTS

| | | |
|---|---|---|
| 3,998,753 A | 12/1976 | Antoshkiw et al. |
| 5,382,714 A | 1/1995 | Khachik |
| 5,648,564 A * | 7/1997 | Ausich et al. ............... 568/834 |
| 5,712,311 A | 1/1998 | Soudant et al. |
| 5,804,168 A | 9/1998 | Murad |
| 5,811,446 A | 9/1998 | Thomas |
| 6,218,436 B1 | 4/2001 | Howard et al. |
| 6,329,557 B1 | 12/2001 | Rodriguez et al. |
| 6,376,722 B1 | 4/2002 | Sanz et al. |
| 6,380,442 B1 * | 4/2002 | Madhavi et al. ............ 568/816 |
| 6,504,067 B1 | 1/2003 | Montoya-Olvera et al. |
| 2004/0258782 A1 | 12/2004 | Hoffman et al. |

FOREIGN PATENT DOCUMENTS

| | | |
|---|---|---|
| EP | 1044954 A1 | 10/2000 |
| WO | WO-04080933 A3 | 9/2004 |

* cited by examiner

*Primary Examiner*—Brian Davis
(74) *Attorney, Agent, or Firm*—Schwegman, Lundberg, Woessner & Kluth P.A.

(57) ABSTRACT

The present invention provides a process for an industrial scale extraction and purification of xanthophylls (e.g., lutein and zeaxanthin) from plant material (e.g., alfalfa or other leafy green crops having high levels of chlorophyll). The process involves harvesting lutein rich alfalfa, extracting an oleoresin from the alfalfa leaves, saponifying the oleoresin, extracting and extracting lutein using a series of solvent extractions specific for oleoresin obtained from alfalfa or other leafy green plants.

66 Claims, 5 Drawing Sheets

ISOLATION OF LUTEIN FROM ALFALFA

RELATED APPLICATIONS

This application is a Continuation of U.S. patent application Ser. No. 10/696,730, filed on Oct. 29, 2003 and issued Sep. 19, 2006 as U.S. Pat. No. 7,109,361, which was a Continuation-In-Part of U.S. patent application Ser. No. 10/688,776, filed on Oct. 17, 2003 now abandoned; which claims priority from U.S. Provisional Application No. 60/452,565, filed on Mar. 7, 2003. These applications are incorporated herein by reference.

BACKGROUND OF THE INVENTION

Carotenoids include hydrocarbons (carotenes) and their oxygenated, alcoholic, derivatives (xanthophylls). Representative examples of carotenes include beta-carotene, alpha-carotene, and lycopene. Representative examples of xanthophylls include lutein, zeaxanthin, capsorubin, capsanthin, astaxanthin, and canthaxanthin. Carotenoids are abundant in fruits and vegetables and have been studied extensively as antioxidants for the prevention of cancer and other human diseases. Among the dietary carotenoids, the focus has been on beta-carotene that has been established to play an important role in the prevention of various types of cancer.

More recent research has shown that other carotenoids, particularly the xanthophylls, posses strong antioxidant capabilities and may be useful in the prevention of diseases including cancer. For example, it has been reported that the consumption of lutein and zeaxanthin leads to a 40 percent reduction in age-related macular degeneration (Seddon et al., 1994, J. Amer. Med. Assoc. 272 (18): 1413-1420). It has also been reported that an increased level of serum carotenoids other than beta-carotene is associated with a lower incidence of heart disease (Morris et al., 1994, J. Amer. Med. Assoc. 272 (18): 1439-1441). The xanthophylls, because of their yellow to red coloration and natural occurrence in human foods, also find uses as food colorants. Thus there is an increasing need for substantially pure xanthophylls, which can be used as nutritional supplements and food additives.

Although present in many plant tissues, carotenoids free of other plant pigments are most readily obtained from flowers (marigold), fruits (berries) and root tissue (carrots and yellow potatoes). Xanthophylls are typically present in plant chromoplasts as long chain fatty esters, typically diesters, of acids such as palmitic and myristic acids.

Although chemical processes for the synthesis of xanthophylls from commercially available starting materials are known, such processes are extremely time-consuming, involve multiple steps, and have not provided an economical process for the production of xanthophylls. A more economical route for the large-scale production of substantially pure xanthophylls is a process that extracts, isolates and purifies xanthophylls from natural sources. However, previous methods that isolate xanthophylls from natural plants suffer from one or more disadvantages. Specifically, previous methods are not suitable for commercial or industrial scale (e.g., about 10,000 lbs of green plants, or more); they do not provide at least about 0.25 kg of lutein and zeaxanthin substantially free (e.g., less than about 25 wt. %) of the lipids/fatty acids; they do not provide xanthophylls suitable for human consumption; they employ solvents and/or reagents that are relatively expensive, as well as relatively unsafe for the environment; they employ relatively large amounts of water; and/or they are carried out employing plants that are not an abundant renewable resource/perennial crop that require relatively low amounts of water, herbicides, pesticides, and fertilizer.

There is a need for a process for obtaining lutein and zeaxanthin (active metabolite of lutein) from green plants, suitable for commercial or industrial scale (e.g., about 10,000 lbs of green plants, or more). The process should provide at least about 0.25 kg of lutein and zeaxanthin substantially free (e.g., less than about 25 wt. %) of the lipids/fatty acids. As such, the lutein and zeaxanthin obtained will preferably include at least about 80 wt. % xanthophylls, suitable for human consumption. The process will preferably employ solvents and reagents that are relatively inexpensive, as well as relatively safe for the environment. The methods will preferably employ relatively low amounts of water. The methods can preferably be carried out employing a plant that is an abundant renewable resource/perennial crop that requires relatively low amounts of water, herbicides, pesticides, and fertilizer.

SUMMARY OF THE INVENTION

The present invention provides a process of obtaining lutein and zeaxanthin (active metabolite of lutein) from green plants, suitable for commercial or industrial scale (e.g., about 10,000 lbs of green plants, or more). When about 10,000 lbs of green plants are employed in the process described herein, about 0.6 lb of natural product is obtained. Of this 0.6 lb of natural product, about 45 wt. % to about 75 wt. % (0.27 lb to 0.45 lb) is lutein; about 5 wt. % to about 10 wt. % (0.03 lb to 0.06 lb) is zeaxanthin; and about 15 wt. % to about 20 wt. % (0.08 lb to 0.12 lb) is lipids/fatty acids. As such, the product obtained from the process described herein will include about 80 wt. % to about 85 wt. % (0.48 lb to 0.51 lb) xanthophylls (lutein and zeaxanthin), suitable for human consumption. The process of the present invention can therefore effectively isolate about 0.45 lb of lutein and about 0.05 lb of zeaxanthin from every 10,000 lbs of green plants. Given that the green plants typically contain about 400 ppm to about 1000 ppm of lutein, on a dry basis, (analyzed by HPLC and GC Mass Spec), the methods of the present invention can effectively isolate about 45 wt. % of the lutein contained within the plant matter.

The methods described herein employ solvents and reagents that are relatively inexpensive, as well as relatively safe for the environment. Specifically, the solvents employed have been used extensively in industries in the United States, can easily be recovered, and reduce VOC air emissions. The methods of the present invention also employ relatively low amounts of water. Reducing water demand and waste water volume reduces the cost of the overall process, as well as provides benefits to the environment.

The methods of the present invention can be carried out employing alfalfa as the plant source. Alfalfa is a renewable resource/perennial crop that requires relatively low amounts of water, herbicides, pesticides, and fertilizer. Alfalfa is also abundant in the United States. When utilizing alfalfa as the plant source, the spent fiber and the spent curd obtained can be used as a livestock feed. The brown liquor by-product obtained can be field applied as a fertilizer or evaporated and used for livestock feed. As such, issues of solid waste can be avoided.

The methods of the present invention provide an opportunity to recover natural beta-carotene as a by-product in the methods described herein (e.g., from the solvent used in the precipitation/crystallization step). The methods of the present invention also provide an opportunity to recover plant lipids such as omega-6 fatty acids as by-product in the methods described herein. Studies have indicated that omega-6 fatty acids may be effective in heart disease prevention.

The present invention provides a method of obtaining a natural product from green plant oleoresin. The method includes (a) saponifying green plant oleoresin to provide a saponified resin; (b) contacting the saponified resin with a first volatile organic solvent to provide a suspension; (c) removing the solids from the suspension to provide a solution; (d) condensing the solution to provide a first oil; and (e) contacting the first oil with a second volatile organic solvent to solidify the natural product (e.g., precipitate the natural product or crystallize the natural product).

The present invention also provides a method of obtaining a natural product from a green plant. The method includes (a) macerating green plants to provide plant matter and juice; (b) separating the plant matter from the juice; (c) heating the juice to coagulate chloroplastic proteins into a green curd; (d) separating the green curd from the juice; (e) optionally drying the green curd; (f) extracting a green plant oleoresin from the green curd employing a first volatile organic solvent; (g) saponifying the green plant oleoresin to provide a saponified resin; (h) contacting the saponified resin with a second volatile organic solvent to provide a suspension; (i) removing the solids from the suspension to provide a solution; (j) condensing the solution to provide a first oil; (k) contacting the first oil with a third volatile organic solvent to solidify the natural product; (l) separating the natural product from the third volatile organic solvent; (m) optionally washing the natural product with water; and (n) optionally drying the washed natural product.

The present invention also provides a natural product obtained from the process of the present invention.

The present invention also provides a pharmaceutical formulation that includes a pharmaceutically acceptable carrier and the natural product obtained from the process of the present invention.

The present invention also provides a neutraceutical formulation that includes a neutraceutically acceptable carrier and the natural product obtained from a process of the present invention.

The present invention also provides a cosmetic formulation that includes a neutraceutically acceptable carrier and the natural product obtained from a process of the present invention.

The present invention also provides a method for treating an ulcer that includes administering an amount of the natural product obtained from a process of the present invention, effective to treat the ulcer.

The present invention also provides a method for treating cancer that includes administering an amount of the natural product obtained from a process of the present invention, effective to treat the cancer.

The present invention also provides a method for treating heart disease that includes administering an amount of the natural product obtained from a process of the present invention, effective to treat the heart disease.

The present invention also provides a method for treating a macular degeneration that includes administering an amount of the natural product obtained from a process of the present invention, effective to treat the macular degeneration.

The present invention also provides a dietary supplement that includes the natural product obtained from a process of the present invention.

The present invention also provides a food product that includes the natural product obtained from a process of the present invention.

The present invention also provides a natural product obtained by the process that includes (a) saponifying green plant oleoresin to provide a saponified resin; (b) contacting the saponified resin with a first volatile organic solvent to provide a suspension; (c) removing the solids from the suspension to provide a solution; (d) condensing the solution to provide a first oil; and (e) contacting the first oil with a second volatile organic solvent to solidify the natural product.

The present invention also provides a natural product obtained by the process that includes (a) macerating green plants to provide plant matter and juice; (b) separating the plant matter from the juice; (c) heating the juice to coagulate chloroplastic proteins into a green curd; (d) separating the green curd from the juice; (e) optionally drying the green curd; (f) extracting a green plant oleoresin from the green curd employing a first volatile organic solvent; (g) saponifying the green plant oleoresin to provide a saponified resin; (h) contacting the saponified resin with a second volatile organic solvent to provide a suspension; (i) removing the solids from the suspension to provide a solution; (j) condensing the solution to provide a first oil; (k) contacting the first oil with a third volatile organic solvent to solidify the natural product; (l) separating the natural product from the third volatile organic solvent; (m) optionally washing the natural product with water; and (n) optionally drying the washed natural product.

By contacting the saponified resin with the first volatile organic solvent (e.g., acetone), a suspension (mixture of solids in a liquid) is formed. These solids can easily be removed from the liquid. The ability and ease in removing these solids contributes to the relatively high yield and purity of the natural product, as well as the ability to use inexpensive and environmentally friendly solvents and reagents. After the solids are removed, the solution can be condensed to form an oil, which can then be contacted with another volatile organic solvent to solidify the natural product. The use of a binary solvent system (e.g., hexanes and chloroform) allows for the efficient separation of lutein and zeaxanthin from the water soluble chlorophyllins, various salts and glycerin. By maintaining a relatively high pH (e.g., $\geq 7$) of the juice, oil, and oleoresin, enzymatic activity is slowed. By maintaining a relatively high pH (e.g., $\geq 10$) of the saponified resin, separation is further enhanced. Again, this contributes to the relatively high yield and purity of the natural product, as well as the ability to use inexpensive and environmentally friendly solvents and reagents.

BRIEF DESCRIPTION OF THE DRAWINGS

Embodiments of the invention may be best understood by referring to the following description and accompanying drawings which illustrate such embodiments. The numbering scheme for the Figures included herein are such that the leading number for a given reference number in a Figure is associated with the number of the Figure. Reference numbers are the same for those elements that are the same across different Figures. For example, a block flow diagram depicting the debris (14) can be located in FIG. 7. However, reference numbers are the same for those elements that are the same across different Figures. In the drawings.

DETAILED DESCRIPTION OF THE PRESENT INVENTION

References in the specification to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The present invention relates to novel methods to obtain a natural product from green plants are provided, as well as novel methods to obtain a natural product from green plant oleoresin. When describing the methods, products obtained from such methods, formulations that include such products, and methods of using such products, the following terms have the following meanings, unless otherwise indicated.

Definitions

As used herein, "natural product" includes naturally occurring compounds in green plants (e.g., alfalfa). The natural product will preferably have biological activity as a pharmaceutical, neutraceutical, cosmeceutical, or a combination thereof. Specifically, the natural product can include xanthophylls (e.g., lutein and/or zeaxanthin).

As used herein, "green plant" includes all organisms commonly known as green algae and land plants, including liverworts, mosses, ferns and other nonseed plants, and seed plants. Specifically, the green plant can be alfalfa.

As used herein, "dry basis" refers to plant matter that is dried to microbial effectiveness (e.g., contains less than about 5 wt. % water).

As used herein, "oleoresin" includes resins and volatile oils in a homogenous mixture. It refers to a natural mixture of a terebinthinate oil and a resin. It includes a liquid or semi liquid preparation extracted (as from capsicum, cubebs, or ginger) by means of a solvent, and consisting of fixed or volatile oil holding resin in solution. Specifically, the oleoresin can be alfalfa oleoresin.

As used herein, "saponifying" includes the process of converting an organic ester into the corresponding alcohol by alkaline hydrolysis.

As used herein, "alkaline metal" includes any of the mono-valent metals of group I of the periodic table (e.g., lithium, sodium, or potassium). The hydroxides of the alkali metals are strongly alkaline (basic).

As used herein, "alkaline earth metal" includes any of the bi-valent metals of group II of the periodic table (e.g., calcium, strontium, barium, or magnesium).

As used herein, "suspension" includes a mixture in which fine particles are suspended in a fluid where they are supported by buoyancy; as well as a mixture in which fine particles are more dense than the fluid and are not supported by buoyancy.

As used herein, "condensing" includes the process of concentrating a solution, or removing at least a substantial portion of organic solvent present in solution, thereby concentrating the solution.

As used herein, "crystallizing" includes the process of forming crystals (crystalline material) of a natural product, from solution.

As used herein, "crystalline includes the regular, geometric arrangement of atoms in a solid.

As used herein, "lutein" refers to a compound having the formula:

which is chemically designated as (3R, 3'R, 6'R)-β,ε-carotene-3,3'-diol. Lutein is a substance of a strongly marked yellow colour, extracted from the yolk of eggs, and from the tissue of the corpus luteum. Lutein is not made in the body and must be obtained from food or vitamin supplements. Lutein is found in large amounts in green, leafy vegetables such as spinach; and legumes such as alfalfa.

The esterified form of lutein refers to a compound having the formula:

wherein $R^1$ and $R^2$ are radicals derived from fatty acids such as palmitic acid.

As used herein, "zeaxanthin" refers to a compound having the formula:

which is chemically designated as beta-carotene-3,3'-diol. Zeaxanthin is a carotene found in corn, fruits, seeds, and egg yolk. As used herein, "xanthophylls" refers to any of several yellow accessory pigments which found in plant leaves, egg yolks and human blood plasma, these pigments are oxygenated derivatives of carotenes and are involved in photosynthesis, for example lutein, violaxanthin and neoxanthine.

As used herein, "fatty acids" refers to organic, monobasic acids derived from hydrocarbons by the equivalent of oxidation of a methyl group to an alcohol, aldehyde, and then acid. Fatty acids can be saturated, unsaturated, or partially unsaturated.

As used herein, "alfalfa" refers to lucern (*Medicago sativa*).

As used herein, "alcohol" includes an organic chemical containing one or more hydroxyl (OH) groups. Alcohols can be liquids, semisolids or solids at room temperature. Common mono-hydroxyl alcohols include, e.g., ethanol, methanol and propanol. Common poly-hydroxyl alcohols include, e.g., propylene glycol and ethylene glycol.

As used herein, "binary solvent system includes a solvent system that includes two components. Each component can include one or more organic solvents. The two components will have markedly differing physical properties (e.g., density, hydrophillicity, solubility, and polarity). The natural product will be more soluble in one of the components (compared to the other component), while the undesirable impurities will be more soluble in the other component (compared to the first component).

As used herein, "straight chain hydrocarbon" includes branched or unbranched organic compounds composed exclusively of carbon and hydrogen where no carbon atoms join to form a ring structure.

As used herein, "decanting" or "decantation" includes pouring off a fluid, leaving a sediment or precipitate, thereby separating the fluid from the sediment or precipitate.

As used herein, "filtering" or "filtration" includes the passage of a liquid through a filter, accomplished by gravity, pressure or vacuum (suction). The filtering effectively separates the sediment or precipitate from the fluid.

As used herein, "centrifuging" or "centrifugation" includes the process of separating fractions of systems in a centrifuge. The most basic separation is to sediment a pellet at the bottom of the tube, leaving a supernatant at a given centrifugal force. In this case sedimentation is determined by size and density of the particles in the system amongst other factors. Density may be used as a basis for sedimentation in density gradient centrifugation. at very high g values molecules may be separated, i.e. Ultra centrifugation. In continuous centrifugation the supernatant is removed continuously as it is formed. It includes separating molecules by size or density using centrifugal forces generated by a spinning rotor. G-forces of several hundred thousand times gravity are generated in ultracentrifugation. Centrifuging effectively separates the sediment or precipitate from the fluid.

As used herein, "curd" includes the coagulated part of any liquid.

As used herein, "polar solvent" includes solvents that exhibit polar forces on solutes, due to high dipole moment, wide separation of charges, or tight association; e.g., water, alcohols, and acids.

As used herein, "macerating" includes softening by steeping in a liquid, with or without heat; to wear away or separate the parts of by steeping; as, to macerate animal or vegetable fiber. Additionally, the term includes physically breaking down the structure of a plant, with or without size reduction. Typically, this is done with a hammer mill. Specifically, the physically breaking down the structure of a plant can be accomplished by cutting, chopping, pressing, and/or grinding the plant.

As used herein, "coagulate" includes converting a fluid or a substance in solution into a curd or solid.

As used herein, "chloroplastic proteins" includes proteins coded by chloroplast genome, which consists of about 100 protein coding genes, 30 tRNAs genes and 4 rRNAs genes. Most chloroplast proteins are coded for by the nuclear genome, synthesized in the cytoplasm and transported into the organelle.

As used herein, "washing" includes contacting a substance (optionally dissolved in an organic solvent) with water, thereby forming two layers (a aqueous layer and an organic layer), optionally mixing and/or shaking, and subsequently separating the two layers. The removal of the aqueous layer from the organic layer brings with it, water-soluble impurities. Alternatively, the term includes the contacting of an organic solid (e.g., crystal) with water to remove water-soluble impurities.

As used herein, "drying" includes removing a substantial portion (e.g., more than 90 wt. %) of the organic solvent and water present therein.

As used herein, "vitamin" refers to an essential low molecular weight organic compound required in trace amounts for normal growth and metabolic processes. They usually serve as components of coenzyme systems. For humans Vitamin A, the B series, C, D1 and D2, E and K are required. Deficiencies of one or more vitamins in the nutrient supply result in deficiency diseases.

As used herein, "mineral" refers to a nutrient required to maintain health.

As used herein, "alpha carotene" refers to a compound of the formula:

As used herein, "beta carotene" refers to a compound of the formula:

As used herein, "vitamin A" refers to a compound of the formula:

which is chemically designated as 3,7-dimethyl-9-(2,6,6-trimethyl-1-cyclohexen-1-yl)-2,4,6,8-nonatetraen-1-ol.

As used herein, "treating" or "treat" includes (i) preventing a pathologic condition (e.g., macular degeneration) from occurring (e.g. prophylaxis); (ii) inhibiting the pathologic condition (e.g., macular degeneration) or arresting its development; and (iii) relieving symptoms associated with the pathologic condition (e.g., macular degeneration).

As used herein, "cancer" includes a type of disease caused by cells that divide and grow uncontrollably, invading and disrupting other tissues and spreading to other areas of the body (metastasis). It is an abnormal uncontrolled growth of tissue that has potential to spread to distant sites of the body. Cancer exerts its deleterious effect on the body by: (a) Destroying the surrounding adjacent tissues: e.g. compressing nerves, eroding blood vessels, or causing perforation of organs; and (b) Replacing normal functioning cells in distant sites: e.g. replacing blood forming cells in the bone marrow, replacing bones leading to increased calcium levels in the blood, or in the heart muscles so that the heart fails.

As used herein, "ulcer" includes a sore, often deep, sometimes inflamed, which heals slowly or not at all.

As used herein, "macular degeneration" includes the breakdown or damage to a portion of the retina known as the macula. Symptoms include blurring of vision (in central visual field), colors appear dim and difficulty reading or performing work up close.

Figure 1:
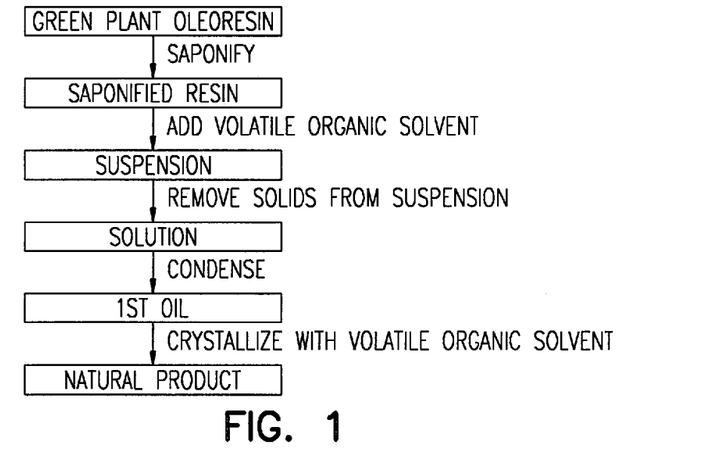
FIG. 1 illustrates a block flow diagram depicting the isolation of a natural product from green plant oleoresin.
Figure 2:
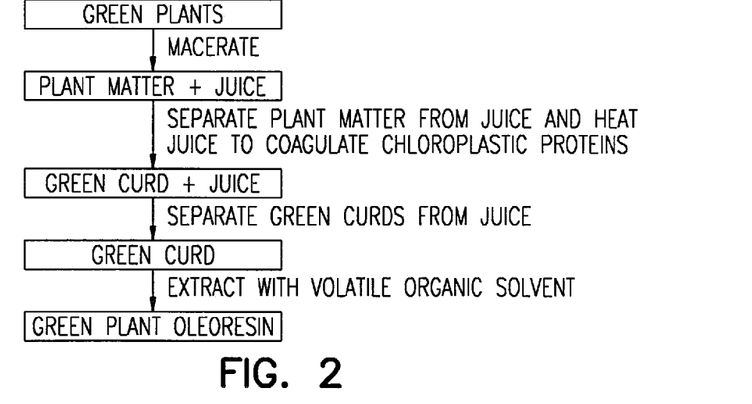
FIG. 2 illustrates a block flow diagram depicting the isolation of green plant oleoresin from green plants.
Figure 3:
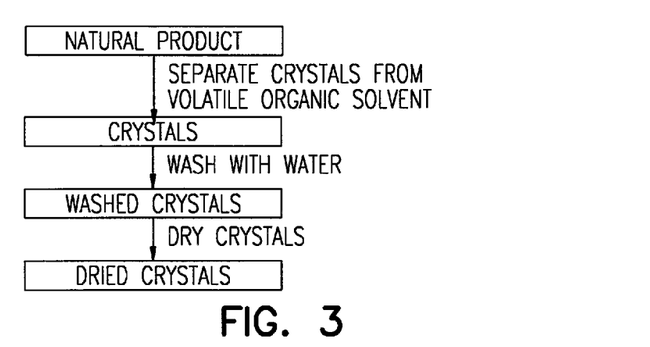
FIG. 3 illustrates a block flow diagram depicting the isolation of dried crystals of a natural product from the natural product material.
Figure 4:
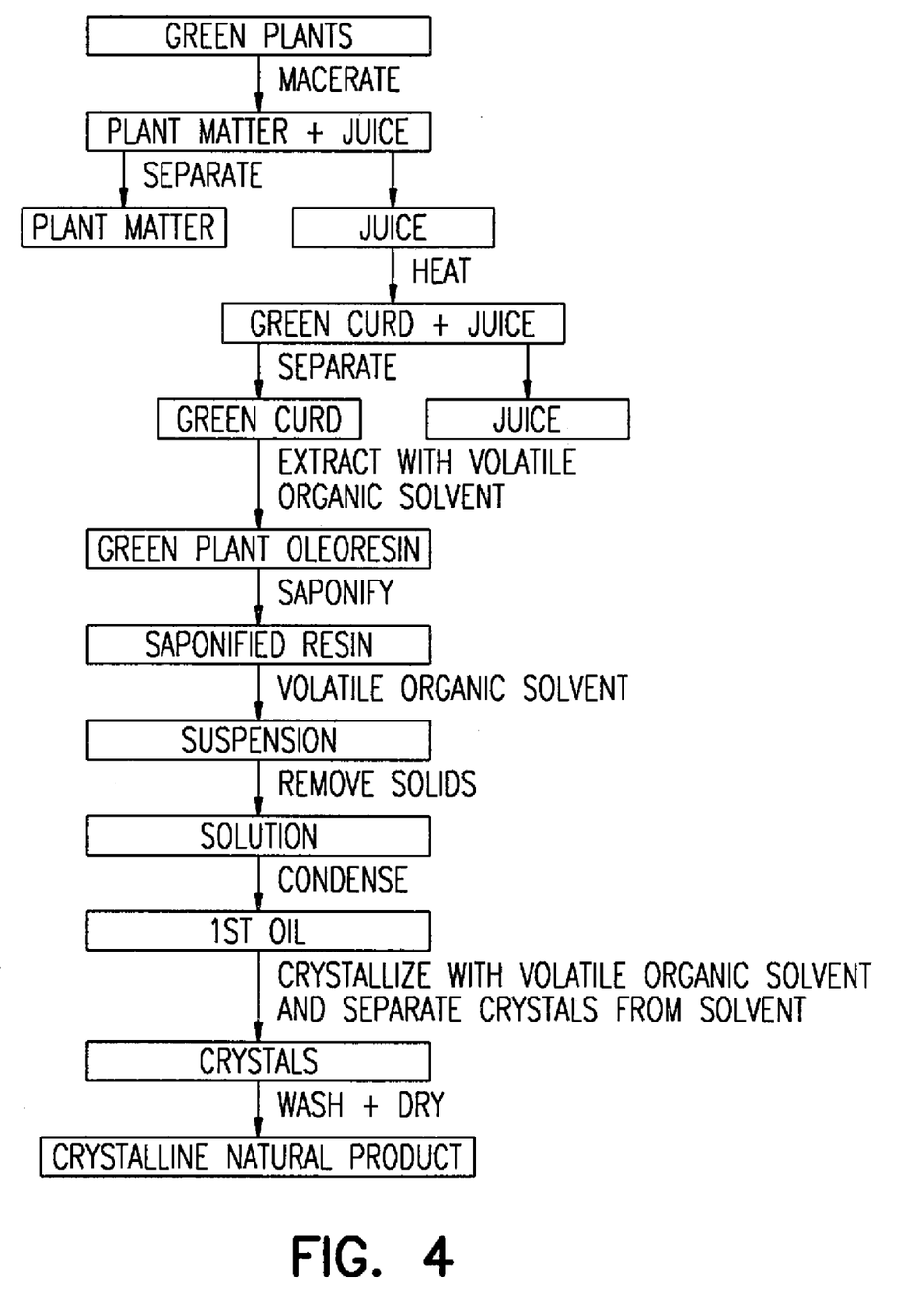
FIG. 4 illustrates a block flow diagram depicting the isolation of crystalline natural product from green plants.
Figure 5:
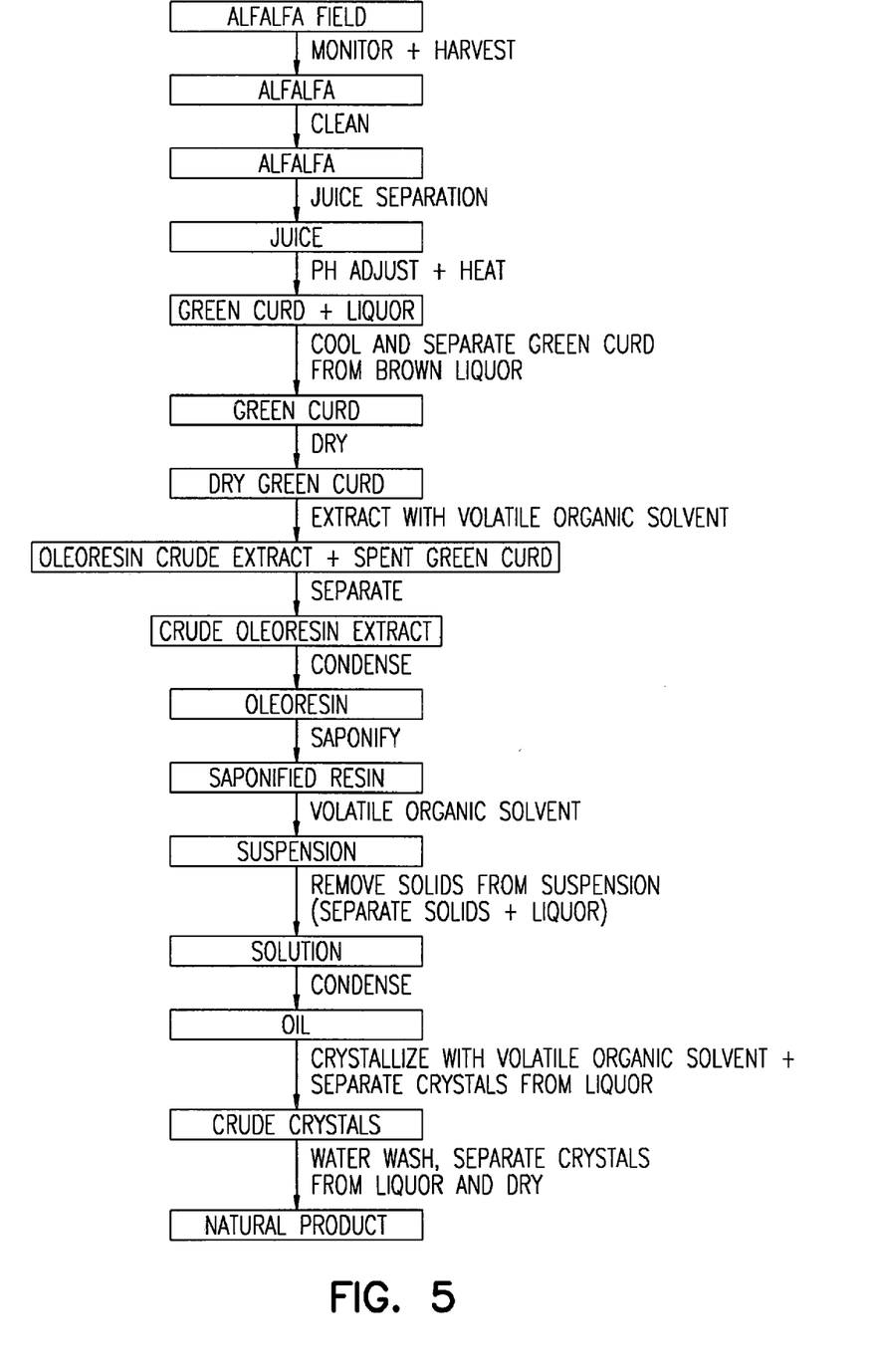
FIG. 5 illustrates a block flow diagram depicting the isolation of a natural product from alfalfa.
Figure 6:
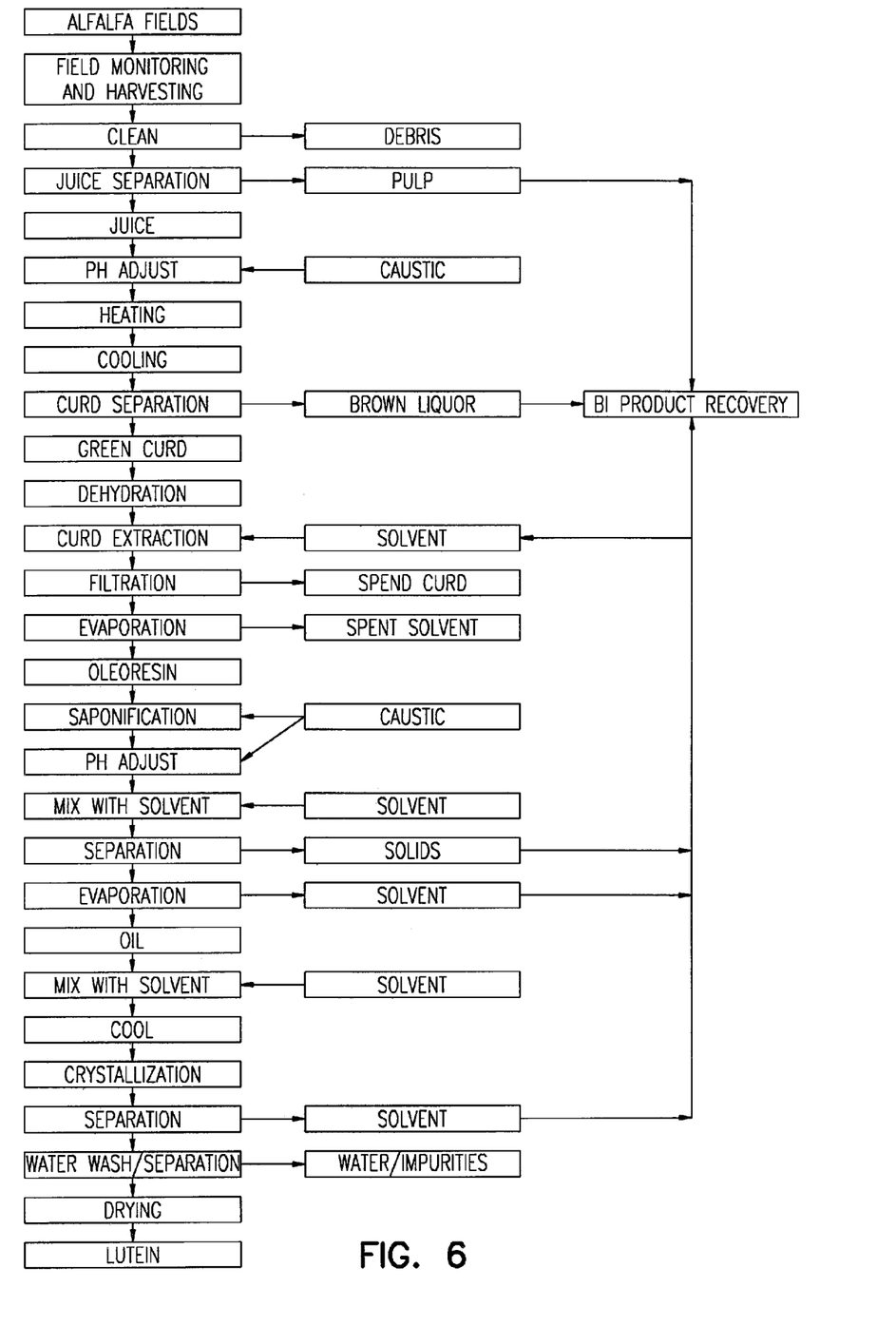
FIG. 6 illustrates a block flow diagram depicting the isolation of lutein from alfalfa.
Figure 7:
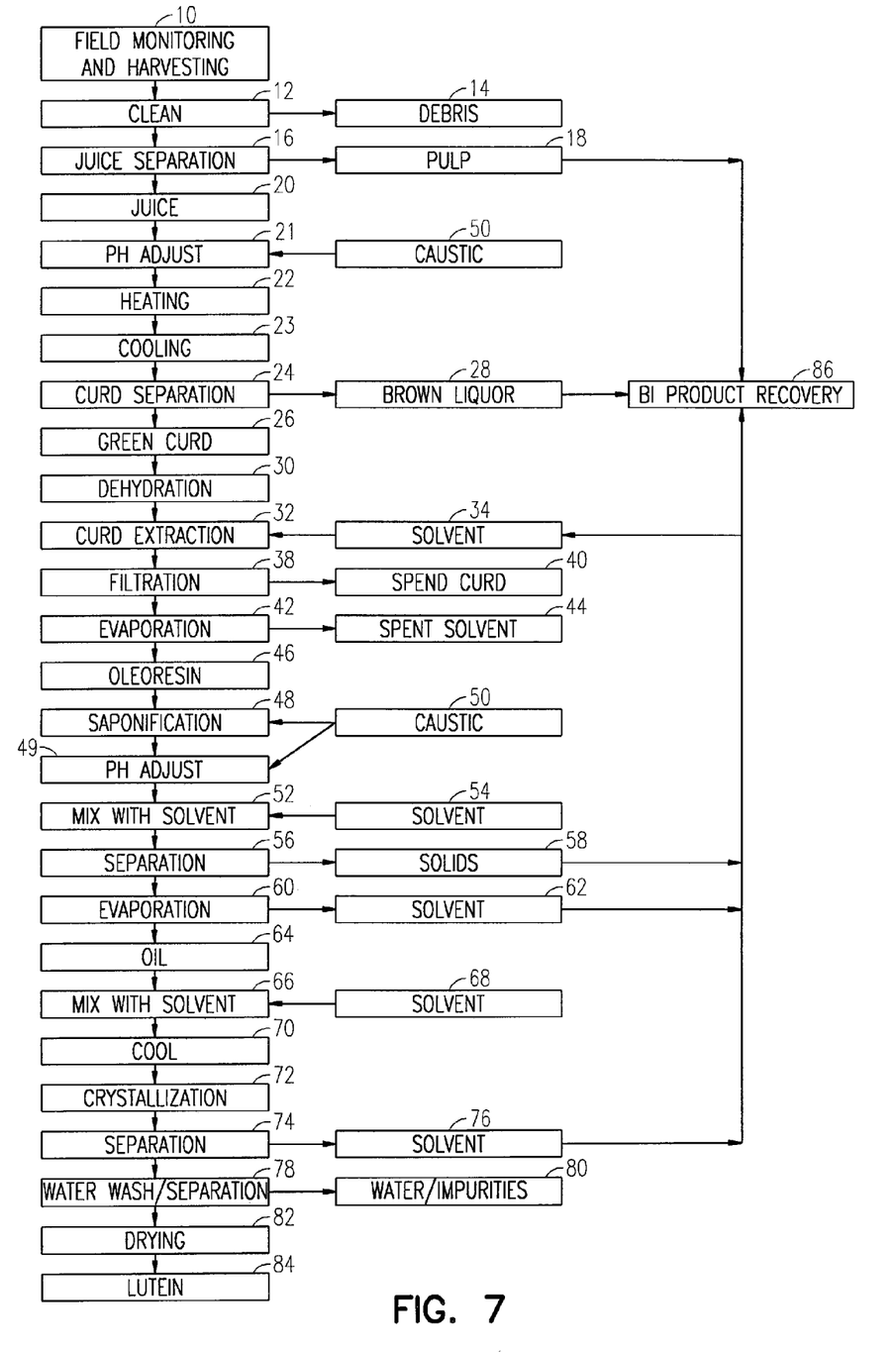
FIG. 7 illustrates a block flow diagram depicting the isolation of lutein.

Referring to FIGS. 1-7, methods to obtain a natural product from green plants are provided, as well as methods to obtain a natural product from green plant oleoresin. The methods of the present invention include field monitoring and harvesting (10) in order to identify fields which will contain sufficient lutein for processing. Preferably, only fields having adequate lutein development are harvested. Generally, alfalfa is considered suitable for lutein extraction prior to developing full blossoms. Such plants are harvested and transported as is commonly known in the art. Harvesting of alfalfa is preferably conducted in a manner that limits leaf loss and crushing, which can reduce the amount of alfalfa juice derived from the process. Monitoring and harvesting are done according to known art using commercially available agricultural equipment that cuts, chops and conveys alfalfa. As is known in the art, cut alfalfa is subject to degradation by enzymes and bacteria. Accordingly, in a preferred embodiment, the process of the present invention minimizes alfalfa degradation by minimizing the time from cutting to processing.

The process of the present invention can be carried out on a large-scale. For example, more than about 5,000 lbs of green plants, more than about 10,000 lbs of green plants, more than about 20,000 lbs of green plants, more than about 50,000 lbs of green plants, more than about 100,000 lbs of green plants, or more than about 200,000 lbs of green plants can be subjected to the processes of the present invention.

Alfalfa can then be cleaned (12). More specifically, the alfalfa can be screened and magnetically separated to remove debris, stones and metal according to methods known in the art. Unwanted debris (14) can be disposed as waste product.

Alfalfa which has had debris removed then undergoes juice separation (16). This step consists of macerating and separating the alfalfa. The extraction of the juice is accomplished by methods known in the art employing, for example, commercial screw presses or belt press for separating alfalfa juice from pulp. Other forms of press systems, known in the art could be utilized to expel alfalfa juice. Pulp (18) can be processed as a by-product for animal feed.

Alfalfa juice (20) obtained from the juice separation (16), contains lutein. The pH is adjusted to about 7.0 to about 8.5 (21). Specifically, the pH can be adjusted to about 7.5. The pH adjustment (21) slows enzymatic activity. In one specific embodiment of the present invention, once the pH has been adjusted, the pH can be maintained above about 7 (e.g., above about 8, above about 9, above about 10, or above about 11) throughout the remainder of the process.

After the pH adjustment (21), the mixture is further processed by heating (22) in order to coagulate chloroplastic proteins. The heating (22) can be conducted at a temperature ranging between about 135° F. and about 200° F., and more specifically between a temperature of about 170° F. and about 180° F. It is believed that heating (22) of the juice slows enzymatic and microbial activity and coagulates chloroplastic proteins into a green curd. The curd juice slurry is cooled (23). The cooling (23) can be accomplished, e.g., within about an hour, within about 30 min, or within about 15 min. Additionally, the curd juice slurry can be cooled (23) to below about 120° F., below about 95° F., or below about 80° F.

The green curd can then be separated (24) from a brown liquor following the cooling (23). Alternatively, (not shown in figures) the green curd can be separated from the brown liquor prior to the cooling (23). Suitable separation (24) techniques include, e.g., centrifugation and filtration. The green curd (26) contains lutein and is further processed as described below. Brown liquor (28) contains relatively no lutein and can be processed as an animal feed by-product. An objective of the present invention is to capture alfalfa chloroplastic protein that is high in pigment. This highly pigmented protein is used in the present invention as a source of alfalfa pigments, specifically lutein and zeaxanthin. As such, the green curd (26) is retained for further processing.

The next step of the process, dehydration (30), involves the drying of the green curd (26). The dehydration (30) can be carried out at any suitable temperature. For example, the dehydration (30) can be carried out below about 180° F. (internal product temperature), below about 150° F. (internal product temperature), or below about 120° F. (internal product temperature). Lower temperatures are preferred to avoid scorching the green curd (26) and to avoid decomposing (e.g., oxidizing) the lutein. When the green curd (26) is dry, it contains about 2 wt. % to about 10 wt. % moisture, about 4 wt. % to about 6 wt. % moisture, or about 5 wt. % moisture.

The green curd (26) is mixed with an organic solvent (34) to extract lutein-containing alfalfa oleoresin into the organic phase. Any suitable organic solvent (34) can be employed provided: (a) lutein is relatively soluble in the organic solvent (34) at standard temperature and pressure; (b) the organic solvent (34) has a suitable boiling point (e.g., 120° F. to about 200° F.), such that the organic solvent (34) can subsequently be removed, e.g., by evaporation; and (c) the formation/existence of an azeotrope is avoided, or at least minimized.

Mixing the green curd (26) with the organic solvent (34) is referred to as the curd extraction (32). Suitable classes of solvents include (with an adjustment in quantity, temperature, pressure and/or exposure duration), e.g., alkanes, cycloalkanes, alkenes, alkynes, halogenated hydrocarbons, alcohols, ethers, aldehydes, ketones, glycols, and aromatic hydrocarbons, alone or in combination thereof. Suitable specific solvents include, e.g., acetone, benzene, chloroform, cyclohexanone, dimethyl sulfoxide, ethyl ether, tetrahydrofuran, methyl tert-butylether, butyl acetate, methyl ethyl ketone (MEK), methylene chloride, and combinations thereof. Additional specific solvents can be found, e.g., in *Aldrich Catalogue of Fine Chemicals*, Milwaukee, Wis. (2003). As noted above, although several solvents may be suitable for the extraction (32), ethyl acetate is utilized in a preferred embodiment of the present invention. In a specific embodiment of the present invention, the organic solvent can be relatively anhydrous (e.g., contains less than 10 wt. % water, less than 5 wt. % or less than 1 wt. % water). For the extraction (32) of lutein from alfalfa, the use of hexane as an oleoresin extraction solvent (34) is not applicable. Hexane should not be used because the lutein is only sparingly soluble in hexane.

The filtration (38) separates the crude oleoresin extract from spent green curd (40). Spent curd (40) contains relatively little lutein, but is high in protein and can be used as a valuable animal feed by-product.

The crude oleoresin extract contains a mixture of xanthophylls, lutein, lipids, pigments, chlorophyllins and organic-soluble residues. The extraction solvent must then be removed from the crude oleoresin extract. The removal of the extraction solvent can be accomplished through the evaporation (42), or any other means as will be known to persons skilled in the art. Evaporated solvent (44) can be recovered and reused. Evaporation (42) of the solvent leads to an oleoresin (46) that is free of solvent (44) and which can be further processed.

In order to further isolate lutein and zeaxanthin from the oleoresin (46), the xanthophylls can be separated from the fatty acids to which they are esterified. This separation is accomplished through aqueous saponification (48) of the oleoresin. Saponification (48) converts lutein esters to free lutein. It also converts chlorophyllins and fatty acids to water-soluble salts. Saponification (48) is achieved by mixing crude oleoresin with an aqueous caustic solution (50). Although a wide range of caustic solutions (50) can be used, a specific embodiment employs 40 wt. % potassium hydroxide in water. Additional aqueous caustic solutions (50) include, e.g., any metal (e.g., potassium, lithium, and sodium) hydroxide, so long as the practitioner employs measures to remove any remaining undesirable metals and/or metal containing salts, after the saponification. Other aqueous caustic solutions (50) include, e.g., ammonia or any amine-based solutions.

In a specific embodiment of the present invention, the solvent employed in the aqueous caustic solution (50) will not include an organic solvent. In another specific embodiment of the present invention, the solvent employed in the aqueous caustic solution (50) will not include an alcohol. In a more specific embodiment of the present invention, the solvent employed in the aqueous caustic solution (50) will not include propylene glycol.

To saponify (48), two parts of crude oleoresin can be mixed with one part of caustic solution. The amount of water present in the reaction mixture can be minimized, but the pH of the mixture should be maintained at about 10 to about 14, about 11 to about 13, or at about 12. The saponification (48) is, at least initially, an exothermic reaction that requires cooling. The reaction mixture should be mixed at an elevated temperature (e.g., up to about 180° F., up to about 160° F., at about 110° F. to about 160° F., or at about 140°

F.). The temperature should be maintained, while mixing, for at least about 0.5 hr, about 0.5 hr to about 2 hr, or for about 1 hr. Individuals skilled in the art will recognize that the saponification (48) does not necessarily need to be held at a specific temperature (e.g., 140° F.) and can be held at a wide range of temperatures from room temperature to about 175° F. If needed, the pH of the saponified resin is adjusted (49) to about 10 to about 14, about 11 to 13, or at about 12. Upon completion of saponification (48), the solution can be cooled to about room temperature.

The saponified resin (52) can be mixed with a volatile organic solvent (54). Any suitable volatile organic solvent (54) can be employed, provided: (a) lutein is relatively soluble in the volatile organic solvent (54) at standard temperature and pressure; and (b) the volatile organic solvent (54) has a suitable boiling point (e.g., 120° F. to about 200° F.), such that the volatile organic solvent (54) can subsequently be removed, e.g., by evaporation. Suitable specific volatile organic solvents (54) include, e.g., acetone, methyl ethyl ketone, ethyl ether, or any combination thereof. In a specific embodiment of the present invention, the volatile organic solvent (54) can be relatively anhydrous (e.g., contains less than 10 wt. % water, less than 5 wt. % or less than 1 wt. % water).

The mixing of the saponified resin (52) and the volatile organic solvent (54) can be carried out up to about 150° F., up to about 120° F., at about 80° F. to about 120° F., or at about 100° F. The ratio of volatile organic solvent (54) to saponified resin (52) can vary. For example, about 10:1 (vol/vol) to about 2,000:1 (vol/vol) of volatile organic solvent (54) to saponified resin (52) can be employed. Specifically, about 100:1 (vol/vol) to about 1,000:1 (vol/vol) of volatile organic solvent (54) to saponified resin (52) can be employed. More specifically, about 100:1 (vol/vol) to about 500:1 (vol/vol) of volatile organic solvent (54) to saponified resin (52) can be employed.

The solvent solution can be separated (56) from the solids (58). Any suitable technique can be employed, e.g., centrifugation, decantation, filtration, or a combination thereof. The solids (58) contain salts, but no lutein or zeaxanthin. As such, the solids (58) can be used as a valuable animal feed by-product.

The volatile organic solvent (54) can be evaporated (60) from the solution, leaving a first oil (64), which contains lutein, zeaxanthin, carotenes, xanthophylls, chlorophyllins, etc. The volatile organic solvent (54) can be recovered and reused (62).

The oil (64) can be mixed (66) with a volatile organic solvent (68). Any suitable volatile organic solvent (68) can be employed, provided: (a) carotene, xanthophylls and chlorophyllins are more soluble than lutein and zeaxanthin, at a ratio of about 10:1 (vol/vol) to about 2,000:1 (vol/vol) of volatile organic solvent (68) to oil (64), at a temperature of about 50° F. to about 130° F.; and (b) the volatile organic solvent (68) has a suitable boiling point (e.g., about 120° F. to about 200° F.).

In one embodiment of the present invention, the volatile organic solvent (68) can be a binary solvent system. The binary solvent system can include, e.g., a first volatile organic solvent in which lutein and zeaxanthin are only slightly soluble and in which carotene, xanthophylls and chlorophyllins are more soluble, at standard temperature and pressure. The binary solvent system can also include, e.g., a second volatile organic solvent in which carotene, xanthophylls and chlorophyllins are only slightly soluble and in which lutein and zeaxanthin are more soluble, at standard temperature and pressure.

In another specific embodiment of the present invention, the volatile organic solvent (68) can be a binary solvent system that includes a first volatile organic solvent (e.g., solvent in which lutein and zeaxanthin are only slightly soluble and in which carotene, xanthophylls and chlorophyllins are more soluble, at standard temperature and pressure) and a second volatile organic solvent (e.g., solvent in which carotene, xanthophylls and chlorophyllins are only slightly soluble and in which lutein and zeaxanthin are more soluble, at standard temperature and pressure). In such an embodiment, the first volatile organic solvent can include, e.g., a straight-chained hydrocarbon, and the second volatile organic solvent can include, e.g., a halogenated solvent. Suitable halogenated solvents include, e.g., chloroform, methylene chloride, and a combination thereof. Suitable straight-chained hydrocarbons include, e.g., hexanes, pentane, or a combination thereof.

In another specific embodiment of the present invention, the volatile organic solvent (68) can be a binary solvent system that includes a first volatile organic solvent (e.g., solvent in which lutein and zeaxanthin are only slightly soluble and in which carotene, xanthophylls and chlorophyllins are more soluble, at standard temperature and pressure) and a second volatile organic solvent (e.g., solvent in which carotene, xanthophylls and chlorophyllins are only slightly soluble and in which lutein and zeaxanthin are more soluble, at standard temperature and pressure). In such an embodiment, the first volatile organic solvent can include, e.g., relatively non polar organic solvent, and the second volatile organic solvent can include, e.g., a relatively polar organic solvent. The non polar organic solvent can be protic or aprotic. Likewise, the polar organic solvent can be protic or aprotic. In one specific embodiment, the first volatile organic solvent can include, e.g., relatively non polar aprotic organic solvent, and the second volatile organic solvent can include, e.g., a relatively polar aprotic organic solvent. Suitable polar and non-polar organic solvent, both protic and aprotic, can be found, e.g., in *Aldrich Catalogue of Fine Chemicals*, Milwaukee, Wis. (2003).

The mixture can then optionally be cooled (70), for example, to about −40° F. to about +30° F. Specifically, the mixture can then be cooled (70) to about −10° F. The lutein and zeaxanthin will crystallize (72) over time from the straight-chained hydrocarbon. The crystals can be separated from the hexane. Any suitable separation technique can be employed, e.g., centrifugation, decantation, filtration, or any combination thereof. The hexane can be recovered for reuse (76).

The crystals can optionally be washed (78) with water to remove the water-soluble impurities (80). The water can have a temperature, e.g., of up to about 150° F., up to about 140° F., up to about 110° F., about 60° F. to about 140° F., or about 90° F. The quantity of the water will typically vary, depending on the nature and amount of impurities and the temperature of the water.

The crystals can optionally be dried (82) to yield substantially free (trans) lutein (84). The free (trans) lutein (84) can be about 50 wt. % to about 90 wt. % pure. Specifically, the crystals can be about 75 wt. % pure free (trans) lutein. The water phase (80) can contain water-soluble components such as chlorophyllin and fatty acid salts, glycerol and other water-soluble compounds that can be used as a valuable animal feed by-product. The crystallization (72) and water washing (78) yields substantially pure lutein (84) suitable for human consumption. The pulp (18), brown liquor (28), and solids (58) can all be recycled as by-products (86) of the process.

Dosage and Formulation

The natural product can be administered as treatment, e.g., for heart disease, macular degeneration, cancer, and related diseases and symptoms, by any means that produces contact of the natural product with the agent's site of action in the body of a mammal. The natural product can be administered by any conventional means available for use in conjunction with pharmaceuticals, either as individual therapeutic agents or in a combination of therapeutic agents. The natural product can be administered alone, but preferably is administered with a pharmaceutical carrier selected on the basis of the chosen route of administration and standard pharmaceutical practice.

The dosage administered will, of course, vary depending upon known factors, such as the pharmacodynamic characteristics of the particular agent and its mode and route of administration; the age, health and weight of the recipient; the nature and extent of the symptoms; the kind of concurrent treatment; the frequency of treatment; and the effect desired. A daily dosage of natural product can be expected to be about 0.001 to about 1000 milligrams per kilogram of body weight, with the preferred dose being about 0.1 to about 100 mg/kg, preferably administered several times a day.

Dosage forms of compositions suitable for administration contain from about 1 μg to about 500 mg of natural product per unit. In these pharmaceutical compositions the natural product will ordinarily be present in an amount of about 0.5-95% by weight based on the total weight of the composition. The natural product can be administered orally in solid dosage forms, such as capsules, tablets and powders, or in liquid dosage forms, such as elixirs, syrups and suspensions. It can also be administered parenterally, in sterile liquid dosage forms. Additives may also be included in the formulation to enhance the physical appearance, improve stability, and aid in disintegration after administration. For example, liquid dosage forms for oral administration can contain coloring and flavoring to increase patient acceptance.

Gelatin capsules contain the natural product and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours or days. Sustained release products can also be formulated for implantation or transdermal/transmucosal delivery. Such formulations typically will include a polymer that biodegrades or bioerodes thereby releasing a portion of the natural product. The formulations may have the form of microcapsules, liposomes, solid monolithic implants, gels, viscous fluids, discs, or adherent films.

Compressed tablets can be sugar coated or film coated to mask any unpleasant taste and protect the tablet from the atmosphere, or enteric coated for selective disintegration in the gastrointestinal tract.

Film-coated tablets are compressed tablets, which are covered with as thin layer of film or water-soluble material. A number of polymeric substances with film-forming properties may be used. Film coating imparts the same general characteristics as sugar coating with the added advantage of a greatly reduced time period required for the coating operation.

Enteric-coated tablets are compressed tablets coated with substances that resist solution in gastric fluid but disintegrate in the intestine. Enteric coatings can be used for tablets containing drug substances which are inactivated or destroyed in the stomach, for those which irritate the mucosa, or as a means of delayed release of the medication.

Multiple compressed tablets are compressed tablets made by more than one compression cycle.

Layered tablets are prepared by compressing additional tablet granulation on a previously compressed granulation. The operation may be repeated to produce multilayered tablets of two or three layers. Special tablet presses are required to make layered tablets.

Press-coated tablets, which are also referred to as drycoated, are prepared by feeding previously compressed tablets into a special tableting machine and compressing another granulation layer around the preformed tablets. They have all the advantages of compressed tablets, i.e., slotting, monogramming, speed of disintegration, etc., while retaining the attributes of sugar-coated tablets in masking the taste of the drug substance in the core tablets. Press-coated tablets can also be used to separate incompatible drug substances; in addition, they can provide a means to give an enteric coating to the core tablets. Both types of multiple-compressed tablets have been widely used in the design of prolonged-action dosage forms.

Compressed tablets can be formulated to release the drug substance in a manner to provide medication over a period of time. There are a number of types which include delayed-action tablets in which the release of the drug substance is prevented for an interval of time after administration of until certain physiological conditions exist; repeat-action tablets which periodically release a complete dose of the drug substance to the gastrointestinal fluids; and the extended-release tablets which continuously release increments of the contained drug substance to the gastrointestinal fluids.

The non-aqueous carrier, or excipient, can be any substance that is biocompatible and liquid or soft enough at the mammal's body temperature to release the natural product into the animal's bloodstream at a desired rate. The carrier is usually hydrophobic and commonly organic, e.g., an oil or fat of vegetable, animal, mineral or synthetic origin or derivation. Preferably, but not necessarily, the carrier includes at least one chemical moiety of the kind that typifies "fatty" compounds, e.g., fatty acids, alcohols, esters, etc., i.e., a hydrocarbon chain, an ester linkage, or both. "Fatty" acids in this context include acetic, propionic and butyric acids through straight- or branched-chain organic acids containing up to 30 or more carbon atoms. Preferably, the carrier is immiscible in water and/or soluble in the substances commonly known as fat solvents. The carrier can correspond to a reaction product of such a "fatty" compound or compounds with a hydroxy compound, e.g., a monohydric, di-hydric, trihydric or other polyhydric alcohol, e.g., glycerol, propanediol, lauryl alcohol, polyethylene or -propylene glycol, etc. These compounds include the fat-soluble vitamins, e.g., tocopherols and their esters, e.g., acetates sometimes produced to stabilize tocopherols. Sometimes, for economic reasons, the carrier may preferably comprise a natural, unmodified vegetable oil such as sesame oil, soybean oil, peanut oil, palm oil, or an unmodified fat. Alternatively the vegetable oil or fat may be modified by hydrogenation or other chemical means which is compatible with the present invention. The appropriate use of hydrophobic substances prepared by synthetic means is also envisioned.

Typically, water, suitable oil, saline, aqueous dextrose (glucose), and related sugar solutions and glycols such as propylene glycol or polyethylene glycols are suitable carriers for parenteral solutions. Solutions for parenteral administration preferably contain a water-soluble salt of the natural product, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts, and sodium EDTA. In addition, parenteral solutions can contain preservatives, such as benzalkonium chloride, methyl- or propyl-paraben and chlorobutanol. Suitable pharmaceutical carriers are described in Remington's Pharmaceutical Sciences, supra, a standard reference text in this field.

In addition to the active or therapeutic ingredient, tablets contain a number of inert materials. The latter are known as additives or "adds." They may be classified according to the part they play in the finished tablet. The first group contains those which help to impart satisfactory compression characteristics to the formulation. These include (1) diluents, (2) binders, and (3) lubricants. The second group of added substances helps to give additional desirable physical characteristics to the finished tablet. Included in this group are (1) disintegrators, (2) colors, and in the case of chewable tablets, (3) flavors, and (4) sweetening agents.

Frequently the single dose of the natural product is small and an inert substance is added increase the bulk in order to make the tablet a practical size for compression. Diluents used for this purpose include dicalcium phosphate, calcium sulfate, lactose, kaolin, mannitol, sodium chloride, dry starch, and powdered sugar.

Most tablet formulators tend to use consistently only one or two diluents selected from the above group in their tablet formulations. Usually these have been selected on the basis of experience and cost factors. However, the compatibility of the diluent with the drug must be considered. When drug substances have low water solubility, it is recommended that water-soluble diluents be used to avoid possible bioavailability problems.

Agents used to impart cohesive qualities to the powdered material are referred to as binders or granulators. They impart a cohesiveness to the tablet formulation which insures the tablet remaining intact after compression, as well as improving the free-flowing qualities by the formulation of granules of desired hardness and size. Materials commonly used as binders include starch, gelatin, and sugars as sucrose, glucose, dextrose, molasses, and lactose. Natural and synthetic gums which have been used include acacia, sodium alginate, extract of Irish moss, panwar gum, ghatti gum, mucilage of isapol husks, carboxymethylcellulose, methylcellulose, polyvinylpyrrolidone, Beegum, and larch arabogalactan. Other agents which may be considered binders under certain circumstances are polyethylene glycol, ethylcellulose, waxes, water and alcohol.

The quality of binder used has considerable influence on the characteristics of the compressed tablets. The use of too much binder or too strong a binder will make a hard tablet which will not disintegrate easily. Alcohol and water are not binders in the true sense of the word; but because of their solvent action on some ingredients such as lactose and starch, they change the powdered material to granules and the residual moisture retained enables the materials to adhere together when compressed.

Lubricants have a number of functions in tablet manufacture. They improve the rate of flow of the tablet granulation, prevent adhesion of the tablet material to the surface of the dies and punches, reduce interparticle friction, and facilitate the ejection of the tablets from the die cavity. Commonly used lubricants include talc, magnesium stearate, calcium stearate, stearic acid, and hydrogenated vegetable oils. Most lubricants with the exception of talc are used in concentrations less than 1%. Lubricants are in most cases hydrophobic materials. Poor selection or excessive amounts can result in "waterproofing" the tablets, result in poor tablet disintegration and dissolution of the drug substance.

A disintegrator is a substance, or a mixture of substances, added to a tablet to facilitate its breakup or disintegration after administration. The natural product must be released from the tablet matrix as efficiently as possible to allow for its rapid dissolution. Materials serving as disintegrates have been chemically classified as starches, clays, celluloses, aligns, or gums.

The most popular disintegrators are corn and potato starch which have been well-dried and powdered. Starch has a great affinity for water and swells when moistened, thus facilitating the rupture of the tablet matrix. However, others have suggested that its disintegrating action in tablets is due to capillary action rather than swelling; the spherical shape of the starch grains increases the porosity of the tablet, thus promoting capillary action.

In addition to the starches a large variety of materials have been used and are reported to be effective as disintegrators. This group includes Veegum HV, methylcellulose, agar, bentonite, cellulose and wood products, natural sponge, cation-exchange resins, alginic acid, guar gum, citrus pulp, and carboxymethylcellulose. Sodium lauryl sulfate in combination with starch also has been demonstrated to be an effective disintegrant.

Colors in compressed tablets serve functions other than making the dosage from more esthetic in appearance. Any of the approved certified water-soluble FD&C dyes, mixtures of the same, or their corresponding lakes may be used to color tablets.

In addition to the sweetness which may be afforded by the diluent of the chewable tablet, e.g. mannitol or lactose, artificial sweetening agents may be included. Among the most promising are two derivatives of glycyrrhizin, the glycoside obtained from licorice.

Compressed tablets may be characterized or described by a number of specifications. These include the diameter size, shape, thickness, weight, hardness, and disintegration time.

Useful pharmaceutical, neutraceutical, and/or cosmeceutical dosage-forms for administration of the natural product can be illustrated as follows:

Capsules

A large number of unit capsules can be prepared by filling standard two-piece hard gelatin capsules each with 100 mg of powdered natural product, 150 mg of lactose, 50 mg of cellulose, and 6 mg magnesium stearic.

Soft Gelatin Capsules

A mixture of natural product in digestible oil such as soybean oil, cottonseed oil or olive oil can be prepared and injected by means of a positive displacement pump into gelatin to form soft gelatin capsules containing 100 mg of the natural product. The capsules should then be washed and dried.

Tablets

A large number of tablets can be prepared by conventional procedures so that the dosage unit is 100 mg of natural product, 0.2 mg of colloidal silicon dioxide, 5 milligrams of magnesium stearate, 275 mg of microcrystalline cellulose, 11 mg of starch and 98.8 mg of lactose.

Suspension

An aqueous suspension can be prepared for oral administration so that each 5 mL contain 25 mg of finely divided natural product, 200 mg of sodium carboxymethyl cellulose, 5 mg of sodium benzoate, 1.0 g of sorbitol solution, U.S.P., and 0.025 mg of vanillin.

Sport Beverage

An aqueous fluid can be prepared for oral administration so that each 355 mL contains 200 mg of finely divided natural product, 250 mg of fructose or sucrose, 5 mg of sodium benzoate, 1 mg of colorant, 5 mg of flavoring agent, and 25 mg of potassium chloride in water (350 ml). Alternatively, the finely divided natural product (200 mg) can be present in orange juice (355 ml).

Injectable

A parenteral composition suitable for administration by injection can be prepared by stirring 1.5% by weight of natural product in 10% by volume propylene glycol and water. The solution is sterilized by commonly used techniques.

Pediatric Dosage

For children, a daily dosage of natural product can be expected to be about 0.001 milligrams per kilogram of body weight to about 100 milligrams per kilogram of body weight, with the preferred dose being about 0.1 mg/kg to about 50 mg/kg, preferably administered several times a day. More specifically, the preferred dose be about 1 mg/kg to about 25 mg/kg, preferably administered several times a day.

Dosage forms of compositions suitable for administration to children will contain from about 1 mg to about 50 mg of natural product per unit. Specifically, the dosage form can contain from about 5 mg to about 25 mg of natural product per unit.

The invention can be described with the following non-limiting example(s).

EXAMPLES

Example 1

Process for the Extraction of Lutein from Alfalfa 10,000 pounds of alfalfa containing 500 ppm of lutein, on a dry basis, were processed according to the disclosed invention. 10,000 pounds is nominally the amount of alfalfa harvested from one acre. After harvesting, the alfalfa was chopped and screened to remove extraneous components, macerated, and the alfalfa juice was expelled. This resulted in 4,000 pounds of pulp and 6,000 pounds of juice. The pH of the juice was adjusted to 7.5 by the addition of 40% aqueous KOH. The quantity of 40% KOH used to adjust the pH was 3.0 gallons. The pH of the fresh, unadjusted juice is about 5.0. The juice was then heated to 180° F. to coagulate chloroplastic protein. The juice/curd slurry was cooled to 80° F. On separation (horizontal bowl decanter centrifuge) of the juice/curd two fractions resulted, 1,500 pounds of wet green curd and 4,500 pounds of brown liquor. The brown liquor contained no detectable lutein and was disposed of as animal feed. The wet curd was dried in an air dryer at 140° F. (product temperature) and yielded 380 pounds of dry green curd. Dry green curd was extracted with 1,500 pounds of food-grade ethyl acetate. Extraction and solvent removal yielded two fractions, 353 pounds of spent curd and 27 pounds of oleoresin. Spent curd contains only a minute amount of lutein and was disposed of as animal feed, after stripping it of residual ethyl acetate.

Evaporation of the oleoresin via a rising film evaporator removed residual ethyl acetate, yielding approximately 27 pounds of oleoresin. A saponification reaction was conducted using 27 pounds of oleoresin mixed with 13 pounds caustic solution consisting of 40% potassium/water by weight. The mixture was vigorously blended at 140° F. for one hour. Saponification was confirmed by chromatography, thus assuring that no lutein esters remained and that the saponification process was complete. After saponification, the pH of the resin was checked and verified it was 12. If the pH was low, 40% aqueous KOH would have been added to bring the pH up to 12.

In the next step, the 40 pounds of saponified resin was mixed with 500 pounds of food grade acetone at 100° F. After blending, the light phase (acetone solution), was separated from the heavy phase (solids) by centrifugation. The acetone was evaporated off yielding 10 pounds of an oil high in lutein, 6%. The oil was mixed with 900 pounds hexane (n-hexane) at room temperature.

The oil/hexane mixture was cooled to −10° F. and crystals were allowed to form. A dark substance eluted from the cooled mixture. The dark substance is believed to consist of water soluble chlorophyllins, various salts and glycerin. The crystals consist mainly of lutein and zeaxanthin. The hexane was removed. The remaining solids, crystals and dark substance were rinsed with water, until the dark substance was not visible. The ratio of rinse water at room temperature used was 50:1, water to solids. The remaining crystals were dried. A chromatograph confirmed that the remaining 0.6 pounds of crystals were about 75% lutein acceptable for human consumption. The remaining 25% was made up of zeaxanthin and other lipids. More specifically, the remaining 0.6 pounds of crystals were about 75% lutein acceptable for human consumption, about 5-10 wt. % zeaxanthin, and about 15-20 wt. % lipids/fatty acids.

Example 2

Alfalfa (575 grams) was processed. Juice was extracted from the alfalfa via a twin-screw juicer. 393 grams of juice and 171 grams of fibrous solids were recovered after juicing. The juice was heated to 200° F. A curd was formed and was separated through a screen from the liquid. 175 grams of curd were recovered. Two tests were performed to try to extract carotenoids from the wet curd with hexane and ethanol was conducted. 20 g of wet curd was added to a flask containing 100 mL of hexane and 20 g of curd were added to a flask containing 100 mL of ethanol. The flasks were held at ambient temperature overnight (15 hours). By visual examination, the hexane was not miscible with the wet curd and no extraction had occurred. A sample of the ethanol was tested by HPLC and found to contain 5-6 ppm lutein. This lutein content is not adequate for a viable production facility (dry curd with 300 ppm is desired).

Example 3

An experiment was conducted to determine effectiveness of different extraction solvents. A Soxlet extractor was used. 13 g of freeze dried curd, produced by juicing alfalfa, heating the juice to 200° F., separating the curd and freeze drying the curd. The solvents tested were THF, Hexane, Dry Ethanol, 95% Ethanol, Ethyl Acetate, and Acetone. The Soxlet extractor was filled with 200 mL of solvent and refluxed for 4 hours. Ethyl Acetate, Hexane and Acetone were the most effective, based on HPLC. The lutein content of these extractants was close to or above 300 ppm.

Example 4

Literature indicates that alfalfa contains lutein esters as well as free (trans) lutein. An experiment was performed to test the free lutein content of samples with and without saponification. 4.39 Kg of alfalfa were processed. Alfalfa juice was extracted via the twin-screw juicer. 2.68 Kg of juice were extracted. The juice was heated to 200° F. and the curd separated via vacuum filter and Buchner funnel. 1.13 Kg of wet curd were recovered. The wet curd was freeze dried. 268 g. of dried curd were recovered. 100 g. of dried green curd was extracted by adding 400 mL of Hexane. This was heated to 110° F. and stirred for 15 minutes. The hexane solution was separated from the solids via vacuum filter and Buchner funnel with #1 Watman filter paper. 200 mL of additional Hexane was added to the solids in a flask. The contents were heated to 110° F. and stirred for 15 minutes. This step was repeated 4 more times. The hexane was removed from the solution via Rotovap. 7.96 g. of an oleoresin were recovered. Samples of the oleoresin, 0.5 g. each were tested. One sample was not saponified and was used as a control. The second sample was mixed with 50 mL of a 10% KOH/Ethanol solution and held at room temperature. The third sample was mixed with 50 mL of the KOH/Ethanol and held at 150° F. for 2 hours. The Fourth sample was mixed with 50 mL of the KOH/Ethanol and held at room temperature for 12 hours. The 4 samples with tested by HPLC. The 12 hour and the heated 2 hours samples yielded lutein (free) contents 180% of the unsaponified and 2 hour room temperature samples.

Example 5

Alfalfa was initially processed, per juice extraction, curd recovery and drying. The dry curd was extracted using ethyl acetate and an oleoresin was recovered. The oleoresin was saponified with a 10% KOH/Ethanol solution. 5 grams of the saponified oleoresin was suspended in 300 mL of water and partitioned with 100 mL of chloroform and this was put in a separatory funnel and vigorously shaken. The separatory funnel was allowed to stand for 14 hours. 5 mL of the lower chloroform layer was removed and centrifuged at 1500 rpm for 30 minutes. 1 mL of the lower layer was removed from the centrifuge tube and assayed for lutein content. The lutein content of this 1 mL sample was found to be 40%, by HPLC.

Example 6

An initial pilot test of the alfalfa process was performed. 7,500 pounds of alfalfa (pre blossom) were harvested. The alfalfa was fed directly from the truck into a Vincent twin screw dewatering press. The alfalfa was not macerated before pressing. Approximately 2000 pounds of juice were recovered. The juice was heated to 160° F. and a curd was formed. The juice/curd mixture was pumped rotary screen/filter equipped with an auger to remove the curd. The rotary filter did not work. Most of the curd was pushed through the filter by the auger. Large screens with cloth were set on barrels and the curd/juice mixture was poured on the filters and let stand. After 8 hours the curd had gathered on top of the screens. The wet curd was removed manually and dried on trays in an oven at 140° F. Approximately 50 pounds of dry curd, at 6% moisture were recovered. The dry curd was extracted with ethyl acetate via a laboratory scale continuous extractor (Crown). Approximately 5 pounds of oleoresin were recovered. Samples of the oleoresin were saponified and found to contain 0.05% lutein, by HPLC. The yield of curd and lutein content of the oleoresin were much lower than the results of laboratory experiments.

Example 7

It was noticed that a significant amount (75-90%) of the lutein was lost between the alfalfa juice and the dry curd. Enzyme activity was suspected. The enzyme suspected was Lipoxygenase. It is most effective at a lower pH and moderately high temperatures. The pH of the alfalfa juice is about 5. A lab experiment was conducted to compare the lutein content of the curd between pH adjusted and unadjusted juice. The juice was extracted from 1700 g of alfalfa. 1240 g of juice was obtained. The pH of the juice was adjusted to 7.5 by the addition of 40% KOH/water. The juice was heated to 200° F. and the wet curd was formed. The curd was separated from the brown juice. 430 g of wet curd was recovered. The wet curd was dried in a food dehydrator. 65 g of dry curd at 5% moisture were recovered. Samples from each step were tested for lutein content. All samples were saponified prior to HPLC analysis, to maximize free lutein content. The alfalfa samples averaged 0.05% lutein, the juice samples 0.15%, the wet curd 0.22% and the dry curd 0.17%. All percentages are on a dry basis. The dry curd without pH adjustment yielded 0.06% lutein.

All publications, patents, and patent documents cited herein are incorporated by reference herein, as though individually incorporated by reference. The invention has been described with reference to various specific and preferred embodiments and techniques. However, it should be understood that many variations and modifications may be made while remaining within the spirit and scope of the invention.

It is appreciated that certain features of the invention, which are, for clarity, described in the context of separate embodiments, may also be provided in combination in a single embodiment. Conversely, various features of the invention which are for brevity, described in the context of a single embodiment, may also be provided separately or in any sub-combination.

The invention claimed is:

1. A method of obtaining xanthophylls from green plant oleoresin, the method comprising:
    (a) saponifying green plant oleoresin to provide a saponified resin, wherein the saponifying employs a saponification agent in an amount sufficient to maintain the pH during the saponifying at about 10 to about 14;
    (b) contacting the saponified resin with a first volatile organic solvent to provide a suspension;
    (c) removing the solids from the suspension to provide a solution;
    (d) condensing the solution to provide a first oil; and
    (e) contacting the first oil with a second volatile organic solvent to solidify the natural product.

2. The method of claim 1 wherein the xanthophylls are in a crystalline form.

3. The method of claim 1 wherein the xanthophylls comprise a mixture of lutein and zeaxanthin.

4. The method of claim 1 wherein the xanthophylls comprise a mixture of lutein crystals and zeaxanthin crystals.

5. The method of claim 1 wherein the xanthophylls comprise about 70 wt. % to about 80 wt. % lutein.

6. The method of claim 1 wherein the xanthophylls comprise about 5 wt. % to about 10 wt. % zeaxanthin.

7. The method of claim 1 wherein the xanthophylls comprise about 70 wt. % to about 80 wt. % lutein and about 5 wt. % to about 10 wt. % zeaxanthin.

8. The method of claim 1 wherein the xanthophylls comprise trans lutein.

9. The method of claim 1 wherein the xanthophylls comprise trans lutein that is at least about 50 wt. % pure.

10. The method of claim 1 wherein the xanthophylls comprise trans lutein that is about 50 wt. % to about 90 wt. % pure.

11. The method of claim 1 wherein at least about 0.5 pounds of xanthophylls are obtained.

12. The method of claim 1 wherein the green plant oleoresin is obtained from alfalfa, clove, kale, spinach, squash, black bean tops, sea-weed, leafy green vegetable, or any combination thereof.

13. The method of claim 1 wherein the green plant oleoresin is obtained from alfalfa.

14. The method of claim 1 wherein the saponifying employs a saponification agent that is an alkali metal hydroxide or an alkaline earth metal hydroxide.

15. The method of claim 1 wherein the saponifying employs a saponification agent selected from the group of sodium hydroxide (NaOH), potassium hydroxide (KOH), and a combination thereof.

16. The method of claim 1 wherein the saponifying employs about 40 wt. % aqueous potassium hydroxide (KOH).

17. The method of claim 1 wherein the saponifying is carried out in the absence of an alcohol.

18. The method of claim 1 wherein the saponifying employs a saponification agent in an amount sufficient to maintain the pH during the saponifying at about 11.5 to about 12.0.

19. The method of claim 1 wherein the saponifying employs a solvent system selected from the group of water, ethanol, methanol, propanol, and any combination thereof.

20. The method of claim 1 wherein the saponifying employs a solvent having at least one hydroxyl group.

21. The method of claim 1 wherein the saponifying is carried out between about 60° F. and about 180° F.

22. The method of claim 1 wherein the saponifying is carried out between about 120° F. and about 160° F.

23. The method of claim 1 wherein the saponifying is carried out for at least about 30 min.

24. The method of claim 1 wherein the saponifying is carried out for about 30 min to about 90 min.

25. The method of claim 1 wherein the volatile organic solvent comprises a compound having at least one carbonyl (C=O) group.

26. The method of claim 1 wherein the volatile organic solvent comprises methyl ethyl ketone (MEK), ethyl acetate, acetone, or any combination thereof.

27. The method of claim 1 wherein the volatile organic solvent comprises a compound having at least one ketone group.

28. The method of claim 1 wherein the first volatile organic solvent comprises acetone.

29. The method of claim 1 wherein the first volatile organic solvent is employed in an amount of about 25:1 (vol/vol) to about 800:1 (vol/vol) of first volatile organic solvent to saponified resin.

30. The method of claim 1 wherein the first volatile organic solvent is employed in an amount of about 50:1 (vol/vol) to about 500:1 (vol/vol) of first volatile organic solvent to saponified resin.

31. The method of claim 1 wherein the saponified resin is contacted with the first volatile organic solvent having a temperature of about 60° F. to about 120° F.

32. The method of claim 1 wherein the solids are removed from the suspension by decantation, filtration, centrifugation, or any combination thereof.

33. The method of claim 1 wherein the second volatile organic solvent is a solvent system wherein carotene, xanthophylls and chlorophyllins are more soluble than lutein and zeaxanthin, at a ratio of about 10:1 (vol/vol) to about 2,000:1 (vol/vol) of second volatile organic solvent to first oil, at a temperature of about 50° F. to about 130° F.

34. The method of claim 1 wherein the second volatile organic solvent is a solvent system wherein carotene, xanthophylls and chlorophyllins are more soluble than lutein and zeaxanthin, at a ratio of about 100:1 (vol/vol) of second volatile organic solvent to first oil, at a temperature of about 72° F.

35. The method of claim 1 wherein the second volatile organic solvent is a binary solvent system.

36. The method of claim 35 wherein the binary solvent system comprises a halogenated organic solvent in which lutein is relatively soluble, and a second organic solvent in which the lutein is relatively insoluble.

37. The method of claim 36 wherein the halogenated organic solvent comprises chloroform.

38. The method of claim 36 wherein the second organic solvent is a straight chain hydrocarbon.

39. The method of claim 38 wherein the straight chain hydrocarbon comprises hexanes.

40. The method of claim 1 wherein the contacting of the first oil and the second volatile organic solvent is carried out at a temperature of about −40° F. to about 30° F.

41. The method of claim 1 wherein the contacting of the first oil and the second volatile organic solvent is carried out at a temperature of about −20° F. to about 0° F.

42. The method of claim 1 further comprising, after the natural product is solidified, separating the natural product from the second volatile organic solvent.

43. The method of claim 1 further comprising, after the natural product is solidified, separating the natural product from the second volatile organic solvent by decantation, filtration, centrifugation, or any combination thereof.

44. The method of claim 42 further comprising, after the natural product is separated from the second volatile organic solvent, washing the natural product with water.

45. The method of claim 44 wherein the water is about 60° F. to about 150° F.

46. The method of claim 44 wherein the water is about 80° F. to about 100° F.

47. The method of claim 44 further comprising, after the washing of the natural product with water, drying the washed natural product.

48. The method of claim 1 further comprising, before saponifying the green plant oleoresin to provide the saponified resin, extracting the green plant oleoresin from a curd employing a third volatile organic solvent.

49. The method of claim 48 wherein the third volatile organic solvent is ethyl acetate, acetone, benzene, chloroform, cyclohexanone, dimethyl sulfoxide, ethyl ether, tetrahydrofuran, methyl tert-butylether, butyl acetate, or combinations thereof.

50. The method of claim 48 wherein the third volatile organic solvent is ethyl acetate.

51. The method of claim 48 wherein the third volatile organic solvent is an aprotic solvent.

52. The method of claim 48 wherein the third volatile organic solvent is a polar solvent.

53. The method of claim 48 wherein the curd is obtained from green plants comprising:
(a) macerating green plants to provide plant matter and juice;
(b) separating the plant matter from the juice;
(c) heating the juice to coagulate chloroplastic proteins into a green curd; and
(d) separating the green curd from the juice.

54. The method of claim 53 wherein the green plants have been macerated within about 1 day of harvesting.

55. The method of claim 53 wherein the heating is carried out at a pH of about 7 to about 8.

56. The method of claim 53 wherein the heating is carried out at a temperature of about 135° F. to about 200° F.

57. The method of claim 53 wherein the heating is carried out at a temperature of about 170° F. to about 190° F.

58. The method of claim 53 wherein after the heating and before the separating, the green curd and the juice is cooled to a temperature of less than about 95° F.

59. The method of claim 53 wherein after the heating and before the separating, the green curd and the juice are cooled to a temperature of less than about 80° F.

60. The method of claim 53 wherein the green curd is separated from the juice by decantation, filtration, centrifugation, or any combination thereof.

61. The method of claim 53 further comprising, after separating the green curd from the juice, drying the green curd.

62. The method of claim 61 wherein the drying is carried out at a temperature of less than about 180° F.

63. The method of claim 61 wherein the drying is carried out at a temperature of less than about 150° F.

64. The method of claim 53 wherein more than about 10,000 pounds of green plants are macerated to provide plant matter and juice.

65. The method of claim 53 wherein at least about 200,000 pounds of green plants are macerated to provide the plant matter and juice.

66. A method of obtaining xanthophylls from a green plant, the method comprising:
(a) macerating the green plant to provide plant matter and juice;
(b) separating the plant matter from the juice;
(c) heating the juice to coagulate chloroplastic proteins into a green curd;
(d) separating the green curd from the juice;
(e) optionally drying the green curd;
(f) extracting a green plant oleoresin from the green curd employing a first volatile organic solvent;
(g) saponifying the green plant oleoresin to provide a saponified resin, wherein the saponifying employs a saponification agent in an amount sufficient to maintain the pH during the saponifying at about 10 to about 14;
(h) contacting the saponified resin with a second volatile organic solvent to provide a suspension;
(i) removing the solids from the suspension to provide a solution;
(j) condensing the solution to provide a first oil;
(k) contacting the first oil with a third volatile organic solvent to solidify the natural product;
(l) separating the natural product from the third volatile organic solvent;
(m) optionally washing the natural product with water; and
(n) optionally drying the washed natural product.

* * * * *

UNITED STATES PATENT AND TRADEMARK OFFICE
CERTIFICATE OF CORRECTION

PATENT NO. : 7,253,294 B2
APPLICATION NO. : 11/463193
DATED : August 7, 2007
INVENTOR(S) : Hoffman et al.

It is certified that error appears in the above-identified patent and that said Letters Patent is hereby corrected as shown below:

In column 6, line 29, after ""crystalline" insert -- " --.

In columns 7-8, line 3 (Structure), delete "  " and insert --  --, therefor.

In column 7, lines 16-21 (Approx.), delete "As used herein, "xanthophylls" refers to any of several yellow accessory pigments which found in plant leaves, egg yolks and human blood plasma, these pigments are oxygenated derivatives of carotenes and are involved in photosynthesis, for example lutein, violaxanthin and neoxanthine." and insert the same on Col. 7, Line 18 (Approx.), below "yolk." as a new paragraph.

In column 9, line 44 (Approx.), delete "cyclohexen" and insert -- cyclohexene --, therefor.

In column 23, line 48, in Claim 24, after "30" delete "min" and insert -- min. --, therefor.

Signed and Sealed this

Fourth Day of March, 2008

JON W. DUDAS
*Director of the United States Patent and Trademark Office*